United States Patent [19]

Freedman et al.

[11] 4,315,929
[45] Feb. 16, 1982

[54] METHOD OF CONTROLLING THE EUROPEAN CORN BORER WITH TREWIASINE

[75] Inventors: Bernard Freedman; Richard G. Powell, both of Peoria; Cecil R. Smith, Jr., Dunlap, all of Ill.

[73] Assignee: The United States of America as represented by the Secretary of Agriculture, Washington, D.C.

[21] Appl. No.: 228,852

[22] Filed: Jan. 27, 1981

[51] Int. Cl.³ .............................................. A01N 43/86
[52] U.S. Cl. ................................................. 424/248.54
[58] Field of Search ................................... 424/248.54

[56] References Cited

U.S. PATENT DOCUMENTS 3,896,111 7/1975 Kupchan ........................... 260/239.3
4,190,580 2/1980 Hashimoto et al. .............. 260/239.3
4,225,494 9/1980 Higashide et al. ................ 260/239.3

OTHER PUBLICATIONS

M. Asai et al., Tetrahedron 35: 1079–1085 (1979).
B. Freedman et al., J. Econ. Entomol. 72: 541–545 (1979).
W. D. Guthrie et al., Proc. Corn Sorghum Res. Conf. 26: 165–179 (1971).
M. C. Wani et al., J.C.S. Chem. Commun., p. 390 (1973).
S. M. Kupchan et al., J. Org. Chem. 42: 2349–2357 (1977).

E. Higashide et al., Nature 270: 721–722 (1977).

*Primary Examiner*—Allen J. Robinson
*Attorney, Agent, or Firm*—M. Howard Silverstein; David G. McConnell; Curtis P. Ribando

[57] ABSTRACT

A novel maytansinoid compound discovered in the seed tissue of Trewia nudiflora has been found to be effective in controlling a common insect pest, the European corn borer. This compound is represented by the formula:

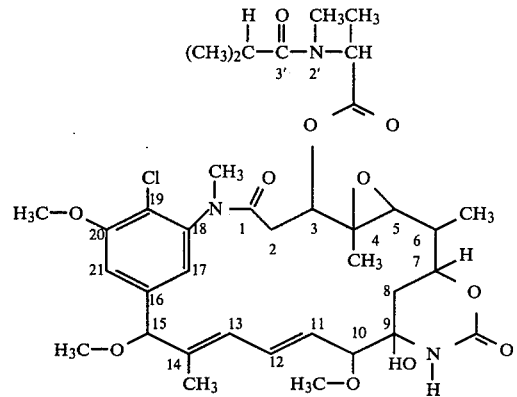

and is characterized by a distinguishing methoxy group on the C-15 carbon.

3 Claims, No Drawings

METHOD OF CONTROLLING THE EUROPEAN CORN BORER WITH TREWIASINE

CROSS-REFERENCE TO RELATED APPLICATION

This application is related to commonly assigned application Ser. No. 228,853, filed concurrently herewith by Richard G. Powell and Cecil R. Smith, Jr. entitled "Chemotherapeutically Active Maytansinoids from *Trewia nudiflora*".

BACKGROUND OF THE INVENTION

1. Field of the Invention

This invention relates to the use of a novel ansa macrolide compound useful as an agent for the control of insect pests.

2. Description of the Prior Art

The isolation of three ansa macrolides from ethanolic extracts of *Maytenus ovatus* and *Maytenus buchananii* was first reported by S. M. Kupchan et al. and is the subject of U.S. Pat. No. 3,896,111. These maytanside esters are characterized by the structural formula

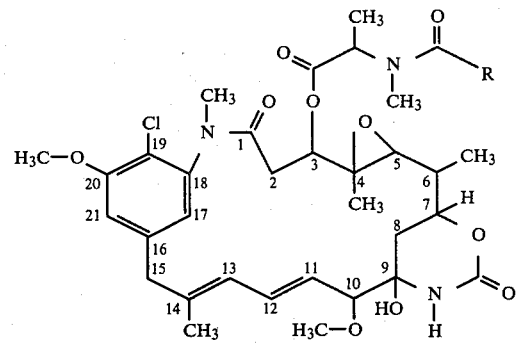

and include maytansine in which R=CH₃, maytanprine in which R=CH₂CH₃, and maytanbutine in which R=CH(CH₃)₂. Kupchan reports that these compounds showed activity against lymphocytic leukemia P388 in test animal tumor systems. Two analogs of maytanbutine isolated from *Colubrina Texensis* are taught by Wani et al. [J.C.S. Chem. Commun., page 390 (1973)] in which the C-15 position bears either an hydroxyl (colubrinol) or an acetate (colubrinol acetate) side chain. These compounds have also demonstrated activity against lymphocytic leukemia P388, and in addition show cytotoxicity (ED₅₀) against KB cell culture. In a later publication by Kupchan et al. [J. Org. Chem. 42: 2349-57 (1977)] a variety of maytansinoids are reviewed and are categorized as either maytanside esters (those having a C-3 ester side chain) or as maytansides (those lacking the C-3 ester side chain). Of particular significance is the disclosure of finding yet another antileukemic principle, maytanbutacine. This maytanside ester was isolated from *Maytenus serrata* and is similar to colubrinol acetate in that it has an acetate side chain in the C-15 position. The difference lies in the C-3 ester group, which is

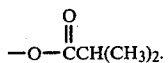

This reference also teaches the isolation of maytansine and related compounds from another celastraceous plant, *Putterlickia verrucosa*. In U.S. Pat. No. 4,190,580, Hashimoto et al. shows that the maytansinoids are also useful as antifungal and antiprotozoan agents.

Higashide et al. [Nature 270: 721-722 (1977) and U.S. Pat. No. 4,225,494] and Asai et al. [Tetrahedron 35: 1079-85 (1979)] first reported the recovery of ansamitocin, a group of ansamycin antibiotics from a fermentation broth of Nocardia sp. No. C-15003 (N-1). The structures of the compounds are similar to maytansine, differing only with respect to the C-3 moiety. Ansamitocin demonstrated strong growth inhibitory activities against phytopathogenic fungi, dermatophytes, and protozoa. Two of the compounds also possess antitumor activity against the P388 strain, as well as significant activity against B16 melanoma, sarcoma 180, Ehrlich carcinoma, and P815 mastocytoma. Some activity was also shown against leukemia L1210.

SUMMARY OF THE INVENTION

We have now unexpectedly discovered that a novel ansa macrolide called trewiasine, which is present in the plant tissue of *Trewia nudiflora* L. and is disclosed in the aforementioned related application, is effective in controlling the European corn borer. Freedman et al. [J. Econ. Entomol. 72: 541-545 (1979)] had previously noted that the ethanolic extract of *Trewia nudiflora* was apparently toxic to the corn borer (Table 2, page 544). However, in view of the known occurrence of the maytansinoids in only a relatively few plant species as described above, and in view of the previously unreported activity of maytansinoids against insects, we were surprised to find that this toxicity was attributed to a maytanside ester. Trewiasine is characterized by a C-15 methoxy side chain not found in any of the previously reported maytansinoids and is represented by the structural formula

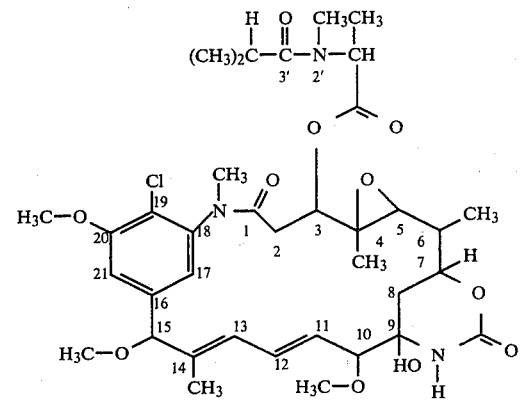

In accordance with this discovery, it is an object of the invention to provide a new and unobvious use for a maytansinoid compound.

It is also an object of the invention to provide a previously unreported maytansinoid as an insect control agent.

It is a further object of the invention to demonstrate the activity of trewiasine against the European corn borer.

Other objects and advantages of this invention will become readily apparent from the ensuing description.

DETAILED DESCRIPTION OF THE INVENTION

The starting material for use in the invention is the seed of *Trewia nudiflora* L. (Euphorbiaceae), and it is considered likely that other tissues of the plant would also contain extractable quantities of the subject compound.

The seed material is prepared for extraction by grinding it in a conventional mill to a suitable particle size, usually in the range of about 0.001–3 mm. in diameter, and more preferably in the range of 0.1–2 mm. The ground material is defatted by extraction with a nonpolar solvent such as hexane, followed by extraction with 95% ethanol or similar polar solvent. The extract is separated from the solid residue and is concentrated to remove the bulk of the solvent, at least to the point of reducing the extract to a thin syrup. The resultant concentrate is partitioned between water and a water-immiscible solvent such as chloroform in order to remove the water solubles. By again concentrating the extract so as to eliminate the majority of the solvent, a crude maytansinoid-containing extract is obtained.

Separation and purification of trewiasine from the crude extract can be effected by the use of proper combination of conventional techniques including, for example, column chromatography (CC), thin-layer chromatography (TLC), and high-pressure liquid chromatography (HPLC). We have successfully employed a sequence of operations comprising: (1) CC on silica; (2) HPLC on silica; and (3) HPLC on a reversed phase ($C_{18}$) column. While not desiring to be limited thereto, the details of the separation procedure as conducted by Powell et al., supra, are illustrated by the following example. Insofar as the instant compound also has chemotherapeutic activity as reported in the aforementioned related application of Powell et al., fractionation of the ethanolic extract was guided by assay against KB cell culture and PS leukemia in mice, with concurrent crosschecking for toxicity against the European corn borer.

EXAMPLE 1

ISOLATION OF COMPOUNDS

A. Approximately 17.2 kg. of *Trewia nudiflora* seed material was ground in a Wiley mill to a particle size of less than about 2 mm. in diameter. The ground material was divided into four batches, each of which was extracted with approximately 32 l. of hexane. A total of 4.07 kg. oil was removed with the hexane fraction, and the four batches of defatted meal were each extracted with approximately 32 l. of 95% ethanol. The extracted residue was discarded and a total of 668 g. of dried material was recovered from the four ethanol fractions. Each fraction was divided in half and partitioned with 1 l. of water and 750 ml. $CHCl_3$ followed by washing the water layer three times with 500 ml. $CHCl_3$. The chloroform fractions and washes from each pair of partitions were combined and taken to dryness and the dried samples representing the four batches were combined into a single crude maytansinoid-containing extract weighing 283.3 g. and identified as F037.

The crude extract (274 g.) was divided in nine portions of approximately 30 g. each and subjected to column chromatography on a column packed with 270 g. of silica. The eluting solvents for each of the nine runs constituted a step-wise gradient of increasing methanol in chloroform, including 1.5 l. $CHCl_3$, 1.5 l. of 5% MeOH in $CHCl_3$, 1.5 l. of 10% MeOH in $CHCl_3$, 1.5 l. of 40% MeOH in $CHCl_3$, and 1.5 l. MeOH. Seven fractions were collected from each run and similar fractions from the nine runs were combined and dried. Chemotherapeutic activity was highest in the fourth fraction, weighing 32.0 g. and identified as F046.

F046 (30.4 g.) was divided into three portions of approximately 10 g. each and chromatographed on silica by preparative HPLC using a step-wise gradient of increasing methanol in dichloromethane. The eluting solvents for each run included 100 ml. $CH_2Cl_2$, 1.5 l. of 2.5% MeOH in $CH_2Cl_2$, 1.5 l. of 5% MeOH in $CH_2Cl_2$, and 2.0 l. of 10% meOH in $CH_2Cl_2$. Eight fractions were obtained from each run and similar fractions were combined and dried. The highest activity was noted in the fifth fraction, weighing 5.3 g. and identified as F093.

The activity of 389 mg. of F093 was further enriched by preparative HPLC on a reversed phase ($C_{18}$) semi-prep column eluted with 30% water in methanol. Six fractions were collected, dried, and identified in the order of collection as F097, F098, K099, K100, F101, and F102. K099 (54 mg.) was recrystallized from $CH_2Cl_2$ to yield a substantially pure compound having a melting point range of 164°–167° C. and designated as trewiasine.

B. F097 (225 mg.) was subjected to HPLC on a reversed phase ($C_{18}$) semi-prep column eluted with 40% water in methanol. Four fractions were collected and dried, the third of which was designated F109. Likewise, a portion of F098 was subjected to HPLC on a reversed phase ($C_{18}$) column eluted with 40% water in methanol. Four fractions were collected and dried, the third of which was designated F105.

3.686 g. of F093, 0.017 g. of F105, and 0.027 g. of F109 were combined, dissolved in $CH_2Cl_2$, and deposited on about 90 cc. of $C_{18}$ silica. The mixture was placed in a precolumn and then subjected to HPLC on a $C_{18}$ prep column eluted with 40% water in methanol. Thirty-one fractions were collected followed by three 1-l. washes with MeOH, $CH_2Cl_2$, and MeOH, respectively. The first MeOH wash was taken to dryness, and 2.18 g. of the resultant sample was redissolved in $CH_2Cl_2$ and deposited on about 90 cc. of $C_{18}$ silica. This material was placed in a precolumn and then subjected to HPLC on a $C_{18}$ prep column eluted with 2 l. 30% $H_2O$ in MeOH, 2.5 l. 20% $H_2O$ in MeOH, 1 l. 100% MeOH, 1 l. 100% $CH_2Cl_2$, and 1.5 l. 100% MeOH. Of 17 fractions collected, the sixth was taken to dryness, yielding 467.0 mg. of material identified as 11399:39-5.

455 mg. of 11399:39-5 was dissolved in $CH_2Cl_2$ at a concentration of approximately 15 mg./100 μl. and was clarified by passing through a plug of cotton to remove 9 mg. of insolubles. The sample was subjected to HPLC on a $C_{18}$ column and eluted with 30% water in methanol. Of four fractions collected, fraction 3 (11399:41-3) was the largest (333.8 mg.).

All of the material obtained above was dissolved in about 4 ml. $CH_2Cl_2$ and triturated with hexane. After standing overnight fluffy needles of pure trewiasine (175 mg.) formed having a m.p. of 176°–179° C. and identified as 11399:41-3A. The mother liquor was triturated with more hexane and 133.6 mg. of precipitate was recovered having a m.p. of 173°–178° C. This sample of trewiasine was slightly less pure than the first recovery, and was identified as 11399:41-3B. Finally, the remaining mother liquor was evaporated to dryness and 18.4 mg. of substantially pure trewiasine was recovered and identified as 11399:41-3C.

The European corn borer, Ostrinia nubilalis (Hübner) of the order Lepidoptera and family Pyralidae is a significant economic pest, destructive to a variety of food crops and ornamental plants. The larva inflicts damage to plants by boring into the stalk, often causing it to collapse or break off. In the case of corn, potatoes, and other crops, the larvae will also bore directly into the food portion, thereby rendering it unmarketable.

In accordance with this invention, the corn borer larvae are controlled by administering trewiasine thereto via the insect's diet. It is therefore envisioned that control will most efficaciously be conducted by applying to the surfaces of susceptible plants an insecticidally effective amount of the pure or substantially pure compound in conjunction with a suitable vehicle or carrier as known in the art. Susceptible plants within the scope of the invention would include all known diets of the European corn borer. While the actual mechanism of killing the insect is not yet understood, the term "insecticidally" is used herein as generally pertaining to the unnatural causation of death in insects. That is, the trewiasine may actually act as an antifeedant, a toxicant, or both. An "insecticidally effective amount" is defined to means those quantities of trewiasine which will result in a significant mortality rate of a test group as compared to an untreated group. A meaningful expression of mortality rate is the percent control, also referred to as "Abbott's formula", and calculated as follows:

$$\% \text{ Control} = \frac{\% \text{ dead (treated group)} - \% \text{ dead (untreated group)}}{100 - \% \text{ dead (untreated group)}} \times 100$$

Any known statistical analysis can be applied to the calculated percent control in order to ascertain whether or not it reflects a significant mortality rate.

The actual effective amount may vary with the stage of larval development, the nature of the substrate, the type of vehicle or carrier, the period of treatment, and other related factors. However, we have found that a significant response will typically be observed for trewiasine levels of at least about 2 p.p.m. of the diet within a 10-day period of treatment. At levels in excess of about 150 p.p.m., 100% control will consistently be achieved within a 10-day treatment period. The $LD_{50}$ of trewiasine against the European corn borer is calculated as 7.4 p.p.m. of the diet and the 95% confidence interval is 4.6–10.6 p.p.m.

EXAMPLE 2

Newly hatched Eurpean corn borer larvae were reared on an artificial agar-based diet prepared by the procedure of Guthrie et al. [Proc. Corn Sorghum Res. Conf. 26: 165–79 (1971)], herein incorporated by reference. For each test treatment, 0.5 ml. of a trewiasine-in-ethanol solution was placed in a jelly cup (36 mm. deep × 26 mm. bottom diameter × 34 mm. top diameter) and allowed to stand overnight to permit the ethanol solvent to evaporate. The same procedure was followed for the controls using pure ethanol. After the solvent had evaporated, 4.0 ± 0.1 g. of the artificial diet was added to each control and test cup and stirred to admix it with the residue. Thereafter, five 7-day-old larvae were placed in each cup and covered with a paper lid lined with "Saran." Four replicate test cups were prepared, each containing 2.5 mg. of trewiasine (K099) from Example 1B. For the controls (untreated), 28 replicate test cups were prepared without any trewiasine. The cups were maintained in an incubator at 27° C. and 70–75% relative humidity with the lights on continuously. They were observed after 5 days and again after 9 days, and the mortality results reported as the percent control as shown in the Table below. Larvae were counted and cumulatively totaled for the replicate test cups. Missing larvae, assumed to have been cannibalized, were omitted from the calculations.

EXAMPLE 3

Example 2 was repeated except that the trewiasine sample was 11399:41-3C from Example 1B, and 16 replicate control cups were used. As in Example 2, four replicate treated cups were tested at each dose level. The results are reported below in the Table.

EXAMPLE 4

Example 2 was repeated except that the trewiasine sample was 11399:41-3A from Example 1B, and 20 replicate control cups were used. Two groups of four replicate treated cups were tested at each dose level. The results are reported below in the Table.

It is understood that the foregoing detailed description is given merely by way of illustration and that modification and variations may be made therein without departing from the spirit and scope of the invention.

TABLE

| | | | Mortality Results | | | | | |
|---|---|---|---|---|---|---|---|---|
| | | | 1st Observation | | | 2nd Observation | | |
| Example | Dose (mg.) | p.p.m.[a] | Days on diet | CD, %[b] | % Control[c,d] | Days on diet | CD, %[b] | % Control[c,d] |
| 2 | 2.5 | 625 | 5 | 3.2 | 79 S | 9 | 7.6 | 100 S |
| 3 | 2.5 | 625 | 3 | 3.9 | 17 G | 10 | 12.1 | 100 S |
| | 1.25 | 312.5 | 3 | 3.9 | 12 | 10 | 12.1 | 100 S |
| | 0.625 | 156.3 | 3 | 3.9 | 7 | 10 | 12.1 | 100 S |
| | 0.313 | 78.1 | 3 | 3.9 | 2 | 10 | 12.1 | 87 S |
| | 0.156 | 39.1 | 3 | 3.9 | 7 | 10 | 12.1 | 81 S |
| 4 | 0.3 | 75 | 5 | 1.1 | 41 S | 11 | 3.4 | 94 S |
| | 0.3 | 75 | 5 | 1.1 | 10 | 11 | 3.4 | 89 S |
| | 0.15 | 37.5 | 5 | 1.1 | 12 G | 11 | 3.4 | 87 S |
| | 0.15 | 37.5 | 5 | 1.1 | 29 S | 11 | 3.4 | 100 S |
| | 0.075 | 18.8 | 5 | 1.1 | 17 G | 11 | 3.4 | 51 S |
| | 0.075 | 18.8 | 5 | 1.1 | 18 G | 11 | 3.4 | 70 S |
| | 0.038 | 9.4 | 5 | 1.1 | 24 S | 11 | 3.4 | 41 S |
| | 0.038 | 9.4 | 5 | 1.1 | 12 | 11 | 3.4 | 59 S |
| | 0.019 | 4.7 | 5 | 1.1 | 9 | 11 | 3.4 | 31 S |
| | 0.019 | 4.7 | 5 | 1.1 | 24 S | 11 | 3.4 | 52 S |

TABLE-continued

| | | | Mortality Results | | | | | |
| --- | --- | --- | --- | --- | --- | --- | --- | --- |
| | | | | 1st Observation | | | 2nd Observation | |
| Example | Dose (mg.) | p.p.m.[a] | Days on diet | CD, %[b] | % Control[c,d] | Days on diet | CD, %[b] | % Control[c,d] |
| | 0.009 | 2.4 | 5 | 1.1 | 35 S | 11 | 3.4 | 44 S |
| | 0.009 | 2.4 | 5 | 1.1 | <0 | 11 | 3.4 | 11 |

[a]Parts trewiasine per million parts diet.
[b]CD, % = % of control insects that are dead.
[c]% Control = % control by Abbott's formula.
[d]S indicates that the mean mortality for that treatment is significantly different from control at P = 0.05, as determined by a range test criterion. G indicates that the mean mortality for that treatment is suggestive of being different from control at P = 0.05, as determined by least significant difference.

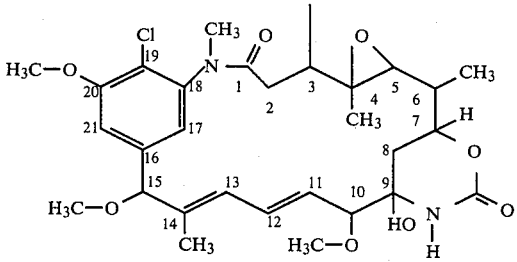

We claim:

1. A method for controlling insect pests, wherein said pests are European corn borers, comprising applying to substrates susceptible to infestation by said pests an insecticidally effective amount of the pure or substantially pure compound of the formula.

2. A method as described in claim 1 wherein said substrates are grain crop plants.

3. A method as described in claim 1 wherein said compound is applied in combination with a suitable carrier.

* * * * *